United States Patent
Pillai et al.

(10) Patent No.: US 6,399,083 B1
(45) Date of Patent: Jun. 4, 2002

(54) COSMETIC COMPOSITIONS CONTAINING CHICK PEA EXTRACT AND RETINOIDS

(75) Inventors: Sreekumar Pillai, Wayne; Manisha Narayan Mahajan, Westwood; Stewart Paton Granger, Paramus; David Joseph Pocalyko, Wayne, all of NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/713,467

(22) Filed: Nov. 15, 2000

Related U.S. Application Data

(60) Provisional application No. 60/165,830, filed on Nov. 16, 1999.

(51) Int. Cl.[7] .............................. A61K 7/00; A61K 7/48; A61K 31/07
(52) U.S. Cl. .................. 424/401; 424/74; 514/783; 514/452
(58) Field of Search .............................. 424/195.1, 401, 424/74; 514/783, 452

(56) References Cited

U.S. PATENT DOCUMENTS

| | | | | |
|---|---|---|---|---|
| 4,761,285 A | | 8/1988 | Vasiliou et al. | 424/195.1 |
| 5,438,073 A | * | 8/1995 | Saurat et al. | 514/452 |
| 6,030,620 A | * | 6/1997 | Pillai et al. | 424/195.1 |
| 5,869,540 A | * | 2/1999 | Smith | 514/783 |
| 6,284,802 B1 | * | 9/2001 | Bissett et al. | 514/739 |

OTHER PUBLICATIONS

J. Invest. Dermatol., Elder et al., vol. 106 pp. 517–521, (1996) Retinoid Induction of CRABP II mRNA in Human Dermal Fibroblasts: Use as a Retinoid Bioassay.

Ingham et al. In: Progress in the Chemistry of Organic Natural Products, vol. 43: Ed–W. Herz et al., Springer Verlag, Wien, New York 1983.

Pharmacological Reviews: 50, 315–333 (1998), Roos et al.

* cited by examiner

*Primary Examiner*—Jose' G. Dees
*Assistant Examiner*—M. Haghighatian
(74) *Attorney, Agent, or Firm*—Ellen Plotkin

(57) ABSTRACT

Cosmetic skin care compositions containing chick pea extract in combination with retinoids.

9 Claims, No Drawings

COSMETIC COMPOSITIONS CONTAINING CHICK PEA EXTRACT AND RETINOIDS

This application claims the benefit of U.S. provisional application No. 60/165,830 filed Nov. 16, 1999.

FIELD OF THE INVENTION

Cosmetic compositions containing chick pea extract in combination with retinoids and methods of conditioning skin by applying such compositions to the skin.

BACKGROUND OF THE INVENTION

Retinol (vitamin A) is an endogenous compound which occurs naturally in the human body and is essential for normal epithelial cell differentiation. Natural and synthetic vitamin A derivatives have been used extensively in the treatment of a variety of skin disorders and as skin repair and renewal agents. Retinoic acid has been used to treat a variety of skin conditions such as acne, wrinkles, psoriasis, age spots and skin discoloration.

Within the cells, retinol and retinoic acid are bound to specific cellular binding proteins, 2 of the major proteins are CRABP-1 and 2 (Roos et al., Pharmacological reviews: 50, 315–333, 1998). These proteins act in regulating the intracellular concentration of retinoids by acting as both storage or shuttle proteins in retinoid metabolism. The levels of this protein are regulated by the amount of retinoic acid within the cells. Higher cellular levels of retinoids increase the expression of CRABP-2. Therefore, the amount of this protein in the cells, is a measure of the retinoid activity of the cells. Skin cells contain CRABP-2 both in the epidermis and the dermis. CRABP-2 response to retinoid administration in fibroblasts in vitro is used as a reproducible measure of retinoid bioactivity that predict human skin responses (Elder et al., J. Invest. Dermatol., 106: 517–521, 1996). Therefore, CRABP-2 expression of fibroblasts is a measure of retinoid activity leading to various cosmetic skin benefits (antiaging, anti wrinkling, skin conditioning etc.).

Chick pea or Spanish pea (*Cicer arietinum*), a common dietary lentil, contains flavonoids including daidzein, formononetin, biochanin A, pratensein, homoferreirin, medicarpin, maackiain, methyl coumestrol, medicagol, formononetin glucoside and biochanin A glucoside (Ingham et al., In: Progress in the chemistry of Organic natural products, vol 43: Ed-W. Herz et al., Springer-Verlag, Wien, N.Y., 1983). The flavonoids from chick pea have been reported to have lipid lowering effects in the blood and liver of rats. Several nutritional studies report on the protein from chick pea for use as nutritional supplements and ways to improve the protein quality of chick pea. Vasiliou, U.S. Pat. No. 4,761,285 discloses the use of chick peas as a dietary supplement or for internal or topical treatment of hemorrhoids. In India, a cosmetic mask or skin treatment made from chick pea powder mixed with water is a common beauty treatment.

The present invention is based in part on the discovery that the organic solvent chick pea extract in combination with retinoids enhances CRABP-2 expression in fibroblasts.

SUMMARY OF THE INVENTION

The present invention includes a cosmetic skin care composition comprising:
(i) a an organic solvent extract of chick pea in an amount of from 0.00001 to 10 wt. %;
(ii) a retinoid in an amount of from 0.001 to 10 wt. %; and
(iii) a cosmetically acceptable vehicle.

The present invention also includes a method of improving or preventing the condition of wrinkled, lined, dry, flaky, aged or photodamaged skin and improving skin thickness, elasticity, flexibility, radiance, glow and plumpness, which method includes applying to the skin the inventive composition. Compositions of the invention are intended for topical application to mammalian skin which is already dry, flaky, lined, wrinkled, aged, photodamaged, or the inventive compositions may be applied prophylactically to reduce the deteriorative changes.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the composition, unless otherwise specified.

Chick peas are suitable for use in the inventive compositions in the form of an organic extract. The chick pea extract is prepared for use in the present invention from dried chick peas. Dried chick peas may be obtained from Arrowhead Mills, from health food stores or supermarket.

The organic chick pea extracts are prepared by extracting the dried chick peas with a solvent by stirring 1 part of dried chick peas with 2 to 5 parts of the solvent for from 4 to 24 hours at room temperature. Suitable solvents are described herein below. The extracts are clarified by filtration and/or centrifugation, then dried by evaporation (optionally, under vacuum) to obtain the organic chick pea extract.

Solvents suitable for the preparation of chick pea extract for use herein include, but are not limited to: ethanol, methanol, hexane, chloroform, dichloromethane and ethyl acetate. The preferred solvents are dichloromethane, methanol, or ethanol in order to optimize activity. The extract may be further concentrated, fractioned, re-extracted or purified, e.g. by organic solvent extraction or by chromatography.

In general, the amount of the chick pea extract in the inventive compositions is in the range of from 0.0001% to 10% by weight composition. Preferably in order to lower cost and maximize the effect the amount of the mulberry extract is in the range of from 0.01 to 10% and most preferably is in the range of from 0.1% to 5%.

The inventive compositions further comprise a retinoid selected from the group consisting of retinol or retinyl ester. The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate.

The preferred ester for use in the present invention is selected from retinyl palmitate, retinyl acetate and retinyl propionate, because these are the most commercially available and therefore the cheapest. Retinyl linoleate is also preferred due to its efficacy.

Retinol or retinyl ester is employed in the inventive composition in an amount of from about 0.001% to about 10%, preferably in an amount of from about 0.01% to about 1%, most preferably in an amount of from about 0.01% to about 0.5%.

The composition according to the invention also comprises a cosmetically acceptable vehicle to act as a diluant, dispersant or carrier for the chick pea extract and the retinoid in the composition, so as to facilitate their distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 $mm^2/s$ (centistokes) at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt. % water, by weight of the vehicle. Preferably, water comprises at least 50 wt. % of the inventive composition, most preferably from 60 to 80 wt. %, by weight of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

The inventive compositions preferably include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Emollients are often incorporated into cosmetic compositions of the present invention. Levels of such emollients may range from 0.5% to 50%, preferably between 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate; and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Use of the Composition

The composition according to the invention is intended primarily as a product for topical cosmetic application to human skin, especially as an agent for conditioning, moisturizing and smoothening the skin, and preventing or reducing the appearance of lined, wrinkled or aged skin.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507, incorporated by reference herein. The invention accordingly also provides a closed container containing a cosmetically acceptable composition as herein defined.

The following specific examples further illustrate the invention, but the invention is not limited thereto. In all examples, chick pea was obtained from local supermarket. Retinoids were obtained from Sigma. Student t-test was used to calculate all p-values.

EXAMPLES

The following methods were employed:
Methods
1. Preparation of Chick Pea Extracts Dried chick pea was purchased from local markets and powdered in a dry grinder. The alcoholic extract of chick pea was prepared by stirring 1 gram of the dry chick pea powder in 10 ml of ethanol for 4 to 24 hrs at room temperature. The extract was clarified by filtration and centrifugation, to obtain a 10% extract of chick pea in ethanol.

2. Cell Culture Method

Human adult fibroblasts obtained from sun-protected inner arm of 25–30 old year female volunteer were used in this. Cells were grown in 1:1 DMEM/Hams F12 media containing 10% FBS, maintained at 37 C. in a 5% CO2 atmosphere under normal atmospheric oxygen tension. Third passage adult fibroblasts were grown in DMEM media with 10% FBS in 12-well plates at a seeding density of 40,000 cells/ml/well. The cells at 80% confluence were rinsed in serum free and phenol red free (PRF) DMEM media twice. Pre-treatment with chick pea extract for 4 hours was conducted and then dosed with retinoids and was incubated for 48 hours. After the incubation, the wells were washed twice with 1×PBS and the cell monolayer was harvested in 100 μl cell lysis buffer (contains 1×PBS, 1% TritonX, 0.5% sodium deoxycholate, 0.1% SDS containing protease inhibitor (10 mg/ml PMSF in isopropanol, 10 μl/ml)). The suspension was spun at 14000 rpm for 10 minutes, the supernatant collected and an aliquot of this supernatant was used for protein quantification. Protein concentration was determined using Pierce protein kit. The remainder of 100 μl supernatant (cell lysate) was denatured in a mixture of 40 μl sample buffer (NOVEX) and 0.5% Beta mercaptoethanol (BME) and by boiling the sample for 5 minutes. Equal amount of protein was then loaded onto 16% Tris-glycine gels for protein analysis by SDS page and Western Immuno-blotting for CRABP-2 protein expression.

3. Detection of Cellular Retinoic Acid Binding Protein 2 (CRABP-2) in Fibroblasts To measure the levels of CRABP-2 in the fibroblasts prepared as described above, the cell supernatant was re-suspended in 4×sample buffer and 0.5% BME, boiled for 5 minutes and used for western blotting. Equal amounts of protein were loaded onto 16% Tris-glycine gels for CRABP-2 protein analysis by SDS page and Western Immuno-blotting. The gels were transferred to nitrocellulose blots and Western Blotting was carried out using monoclonal antibodies to CRABP-2 according to standard procedures. The CRABP-2 protein band was visualized in the Western Blots using the chemiluminescence system obtained from Santa Cruz Biotechnology (Santa Cruz, Calif.). The bands in the film were quantitated by densitometric scanning, the data from triplicate samples were calculated as % of control and expressed in the following tables as % increase over control (with control as 100%) +/−SD of triplicates.

Examples 1–4

The examples investigated the effect on CRABP-2 expression of fibroblasts of combinations of various concentrations of chick pea extract and retinoids.

EXAMPLE 1

| Groups | CRABP-2 levels | As % of control | p value vs. control | p value vs. retinoid | p value vs. Chick pea | Synergy |
|---|---|---|---|---|---|---|
| Control | 0.7 +/− 0.2 | 100 +/− 29 | 1 | | | |
| Retinol | 2.02 +/− 0.23 | 289 +/− 34 | 0.0000056 | 1 | | |
| Retinyl Palmitate | 1.84 +/− 0.16 | 262 +/− 24 | 0.00053 | 1 | | |
| Retinyl linoleate | 2.06 +/− 0.09 | 294 +/− 12 | 0.0000014 | 1 | | |
| Retinyl acetate | 1.44 +/− 0.26 | 206 +/− 37 | 0.0022 | 1 | | |
| Chick pea ext. | 1.71 +/− 0.09 | 245 +/− 13 | 0.00010 | | | |
| Chick pea + retinol | 3.38 +/− 0.22 | 482 +/− 32 | 4.4E −07 | 0.00208 | 0.000031 | Yes |
| Chick pea + ret. palmitate | 1.85 +/− 036 | 264 +/− 52 | 0.000113 | 0.975 | 0.564 | No |
| Chick pea + ret. Linoleate | 1.89 +/− 0.19 | 270 +/− 28 | 0.000075 | 0.256 | 0.23 | No |
| Chick pea + ret. acetate | 3.72 +/− 1.06 | 532 +/− 151 | 0.0000177 | 0.022 | 0.030 | Yes |

100 nM retinoids and 0.1 μl of a 10% chick pea extract

EXAMPLE 2

100 nM retinoids and 1.0 μl of a 10% chick pea extract

| Groups | CRABP-2 levels | As % of control | p value vs. control | p value vs. retinoid | p value vs. Chick pea | Synergy |
|---|---|---|---|---|---|---|
| Control | 0.7 +/− 0.2 | 100 +/− 29 | 1 | | | |
| Retinol | 2.02 +/− 0.23 | 289 +/− 34 | 0.0000056 | 1 | | |
| Retinyl Palmitate | 1.84 +/− 0.16 | 262 +/− 24 | 0.00053 | 1 | | |
| Retinyl linoleate | 2.06 +/− 0.09 | 294 +/− 12 | 0.0000014 | 1 | | |
| Retinyl acetate | 1.44 +/− 0.26 | 206 +/− 37 | 0.0022 | 1 | | |
| Chick pea ext. | 1.46 +/− 0.37 | 209 +/− 54 | 0.0049 | | | |
| Chick pea + retinol | 5.52 +/− 0.02 | 789 +/− 3.0 | 7.3E−08 | 0.000293 | 7.3E−04 | Yes |
| Chick pea + ret. palmitate | 3.24 +/− 0.42 | 462 +/− 60 | 0.0000019 | 0.049 | 0.016 | Yes |
| Chick pea + ret. Linoleote | 3.69 +/− 1.5 | 527 +/− 223 | 0.00167 | 0.147 | 0.075 | No |
| Chick pea + ret. acetote | 3.48 +/− 0.21 | 498 +/− 30 | 2.88E−07 | 0.00047 | 0.0012 | Yes |

EXAMPLE 3

500 nM retinoids and 0.1 μl of a 10% chick pea extract

| Groups | CRABP-2 levels | As % of control | p value vs. control | p value vs. retinoid | p value vs. Chick pea | Synergy |
|---|---|---|---|---|---|---|
| Control | 0.7 +/− 0.2 | 100 +/− 29 | 1 | | | |
| Retinol | 0.72 +/− 0.04 | 102 +/− 6 | 0.877 | 1 | | |
| Retinyl Palmitate | 0.94 +/− 0.31 | 135 +/− 45 | 0.196 | 1 | | |
| Retinyl linoleate | 0.81 +/− 0.16 | 115 +/− 23 | 0.455 | 1 | | |
| Retinyl acetate | 1.65 +/− 0.49 | 235 +/− 70 | 0.0057 | 1 | | |
| Chick pea ext. | 1.71 +/− 0.09 | 245 +/− 13 | 0.00010 | | 1 | |
| Chick pea + retinol | 0.74 +/− 0.22 | 106 +/− 31 | 0.78 | 0.86 | 0.0021 | No |
| Chick pea + ret. palmitate | 2.63 +/− 0.58 | 376 +/− 83 | 0.0000124 | 0.0118 | 0.045 | Yes |
| Chick pea + ret. Linoleote | 3.83 +/− 1.79 | 547 +/− 256 | 0.00026 | 0.043 | 0.011 | Yes |
| Chick pea + ret. acetote | 6.31 +/− 1.63 | 901 +/− 233 | 4.5E−05 | 0.033 | 0.0082 | Yes |

EXAMPLE 4

500 nM retinoids and 1.0 μl of a 10% chick pea extract

| Groups | CRABP-2 levels | As % of control | p value vs. control | p value vs. retinoid | p value vs. Chick pea | Synergy |
|---|---|---|---|---|---|---|
| Control | 0.7 +/− 0.2 | 100 +/− 29 | 1 | | | |
| Retinol | 0.72 +/− 0.04 | 102 +/− 6 | 0.877 | 1 | | |
| Retinyl Palmitate | 0.94 +/− 0.31 | 135 +/− 45 | 0.196 | 1 | | |
| Retinyl linoleate | 0.81 +/− 0.16 | 115 +/− 23 | 0.455 | 1 | | |
| Retinyl acetate | 1.65 +/− 0.49 | 235 +/− 70 | 0.0057 | 1 | | |
| Chick pea ext. | 1.71 +/− 0.09 | 245 +/− 13 | 0.00010 | | 1 | |
| Chick pea + retinol | 3.19 +/− 0.14 | 456 +/− 20 | 3.53E−07 | 9.45E−06 | 0.0018 | Yes |
| Chick pea + ret. palmitate | 2.78 +/− 0.11 | 393 +/− 15 | 1.02E−06 | 0.000733 | 0.0047 | Yes |
| Chick pea + ret. Linoleote | 3.43 +/− 0.26 | 490 +/− 37 | 5.7E−07 | 0.000132 | 0.0018 | Yes |
| Chick pea + ret. acetate | 3.74 +/− 0.09 | 534 +/− 13 | 6.27E−08 | 0.0044 | 0.00054 | Yes |

The results summarized in Examples 1–4 demonstrate that retinoids at some concentrations synergize with chick pea extract at some concentrations. Optimum synergy was observed with all the retinoids at 500 nM level and 1 μl of chick pea extract.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic skin care composition comprising:
   (i) an organic solvent extract of chick pea in an amount of from 0.00001 to 10 wt. %,
   (ii) a retinoid selected from the group consisting of retinol and retinyl esters in an amount of from 0.001 to 10 wt. %; and
   (iii) a cosmetically acceptable vehicle.

2. A cosmetic method of improving the appearance of wrinkled, lined, dry, flaky, aged or photodamaged skin and improving skin thickness, elasticity, flexibility and plumpness, the method comprising applying to the skin the composition of claim 1.

3. A cosmetic method of increasing the level of cellular retinoic acid binding protein in the skin fibroblasts, the method comprising applying to the skin the composition of claim 1.

4. The cosmetic skin care composition according to claim 1 wherein the retinoid is retinol.

5. The cosmetic skin care composition according to claim 1 wherein the retinoid is retinyl palmitate; and wherein said retinyl palmitate is present in an amount such as to provide a retinoid activity equivalent to greater than 100 nM.

6. The cosmetic skin care composition according to claim 1 wherein the retinoid is retinyl linoleate; and wherein said retinyl linoleate is present in an amount such as to provide a retinoid activity equivalent to greater than 100 nM.

7. The cosmetic skin care composition according to claim 1 wherein the retinoid is retinyl acetate.

8. A cosmetic method of improving the appearance of wrinkled, lined, dry, flaky, aged or photodamaged skin and improving skin thickness, elasticity, flexibility and plumpness, the method comprising applying to the skin the composition of claim 7.

9. A cosmetic method of increasing the level of cellular retinoic acid binding protein in the skin fibroblasts, the method comprising applying to the skin the composition of claim 7.

* * * * *